United States Patent
Winslow

(10) Patent No.: US 7,241,314 B1
(45) Date of Patent: Jul. 10, 2007

(54) REVERSE SHOULDER PROSTHESIS

(75) Inventor: Nathan A Winslow, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 100 days.

(21) Appl. No.: 10/943,036

(22) Filed: Sep. 16, 2004

(51) Int. Cl.
*A61F 2/40* (2006.01)

(52) U.S. Cl. .................................. 623/19.13

(58) Field of Classification Search .. 623/19.11–19.14, 623/20.11, 20.22, 20.35, 20.36, 21.13, 22.15, 623/22.11, 22.21, 22.4, 23.15, 23.4
See application file for complete search history.

(56) References Cited

U.S. PATENT DOCUMENTS

| 3,978,528 | A | | 9/1976 | Crep | |
|---|---|---|---|---|---|
| 4,693,723 | A | | 9/1987 | Gabard | |
| 4,964,865 | A | * | 10/1990 | Burkhead et al. | 623/19.11 |
| 5,032,132 | A | * | 7/1991 | Matsen et al. | 623/19.11 |
| 5,080,673 | A | * | 1/1992 | Burkhead et al. | 623/19.11 |
| 5,489,310 | A | * | 2/1996 | Mikhail | 623/19.11 |
| 5,723,018 | A | | 3/1998 | Cyprien et al. | |
| 6,406,495 | B1 | * | 6/2002 | Schoch | 623/19.13 |
| 6,530,957 | B1 | * | 3/2003 | Jack | 623/19.14 |
| 6,736,851 | B2 | * | 5/2004 | Maroney et al. | 623/19.12 |
| 6,761,740 | B2 | * | 7/2004 | Tornier | 623/19.13 |
| 6,887,277 | B2 | * | 5/2005 | Rauscher et al. | 623/19.13 |
| 6,899,736 | B1 | * | 5/2005 | Rauscher et al. | 623/19.12 |
| 6,953,478 | B2 | * | 10/2005 | Bouttens et al. | 623/19.11 |
| 2003/0055507 | A1 | * | 3/2003 | McDevitt et al. | 623/19.11 |
| 2003/0114933 | A1 | | 6/2003 | Bouttens et al. | |
| 2003/0158605 | A1 | | 8/2003 | Tornier | |
| 2004/0039449 | A1 | * | 2/2004 | Tornier | 623/19.13 |
| 2004/0064190 | A1 | * | 4/2004 | Ball et al. | 623/19.14 |
| 2004/0220673 | A1 | * | 11/2004 | Pria | 623/19.12 |
| 2005/0261775 | A1 | * | 11/2005 | Baum et al. | 623/19.12 |
| 2005/0278031 | A1 | * | 12/2005 | Tornier et al. | 623/19.12 |
| 2005/0278032 | A1 | * | 12/2005 | Tornier et al. | 623/19.12 |
| 2006/0020344 | A1 | * | 1/2006 | Shultz et al. | 623/19.12 |

FOREIGN PATENT DOCUMENTS

WO    WO 02/067821 A2    6/2002

OTHER PUBLICATIONS

Encore Surgical; "Reverse Shoulder Prosthesis"; 2 pgs.
Canada News Wire; The Power to be Heard; "First North American Reverse Shoulder Replacement Surgery Performed at Toronto Western Hospital"; Mar. 25, 2004; 2 pgs.

* cited by examiner

*Primary Examiner*—Alvin J. Stewart
(74) *Attorney, Agent, or Firm*—Harness, Dickey & Pierce, P.L.C.

(57) ABSTRACT

A reverse shoulder prosthesis. The reverse shoulder prosthesis includes a humeral socket having a concave surface, and a glenoid component having a major diameter and a convex surface for articulating with the concave surface of the socket. The convex surface has a height from the major diameter that is less than a corresponding spherical surface height.

30 Claims, 3 Drawing Sheets

$f(x) = \dfrac{1}{1 - 0.2x}$

REVERSE SHOULDER PROSTHESIS

Traditional shoulder joint replacement provides a ball and socket implant with a metal ball replacing the humeral head and a glenoid socket attached to the scapula. The traditional ball and socket implant can work properly when the rotator cuff muscles are substantially intact and function to provide stability against displacement of the ball relatively to the socket by the strong deltoid muscle during movement of the shoulder. Patients with rotator cuff impairment can be provided with a reverse ball and socket prosthesis in which the socket is attached to the humeral implant and the ball ("glenosphere") is attached to the scapula. The reverse ball and socket prosthesis cooperates with the deltoid muscle to provide shoulder mobility, is sufficiently stable and does not rely on a functioning rotator cuff for stability. As in traditional shoulder prosthesis, however, loosening of the glenoid component can be a long term concern.

There is, therefore, a need for reverse shoulder implants that reduce the incidence of glenoid loosening.

SUMMARY

The present teachings provide a reverse shoulder prosthesis. The reverse shoulder prosthesis includes a humeral socket having a concave surface, and a glenoid component having a major diameter and a convex surface for articulating with the concave surface of the socket. The convex surface has a height from the major diameter that is less than a corresponding spherical surface height. The convex surface can be, for example, ovoid.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses.

Figure 1:
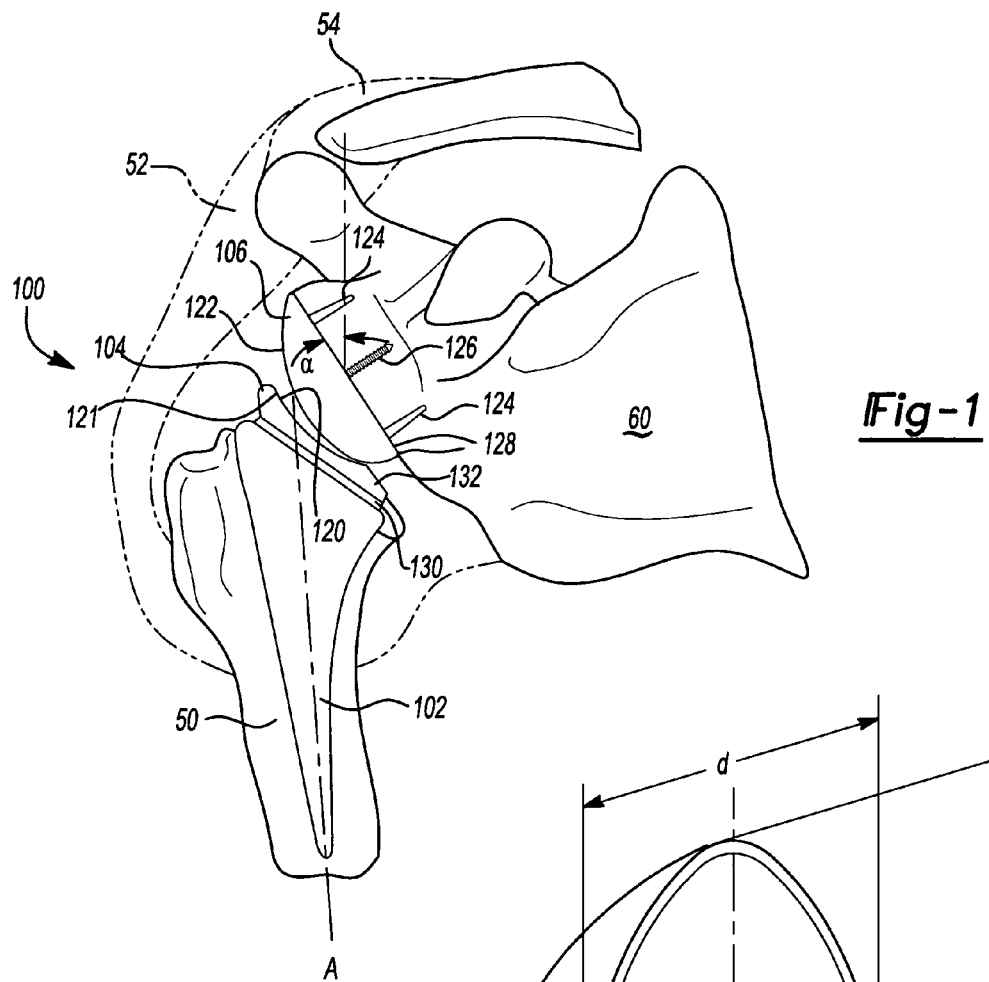
FIG. 1 is an environmental view of a reverse shoulder prosthesis according to the present teachings.

Referring to FIG. 1, an exemplary reverse shoulder prosthesis 100 according to the present teachings includes a glenoid component 106, a humeral stem 102, and a humeral socket 104 attached to the humeral stem 102. The glenoid component 106 functions as a "glenosphere", but is ovoid (egg-shaped), or similarly shaped, and not spherical. The humeral stem 102 is implanted into the humerus 50, and the humeral socket 104 is attached to the humeral stem 102 by male-female Morse tapers, fasteners or other known means of attachment. The humeral socket 104 can be an integral component made of various biocompatible materials, such as, for example, titanium alloys or other metals, polyethylene, ceramic, diamond, etc., and combinations thereof. In other aspects, the humeral socket 104 can be modular including, for example, a backing plate 130 and an insert 132. The humeral socket 104 can be, optionally, integral with the humeral stem 102. The glenoid component 106 can be made of various biocompatible materials including, for example, ceramic, diamond, titanium alloys, cobalt chromium alloys, and other metals.

The humeral socket 104 has a concave articulating surface 120. The concave articulation surface 120 can have a spherical portion, with a constant radius of curvature or can be a curved surface with a variable radius of curvature, or can be a combination of surfaces with different curvatures, including flat portions.

Figure 2A:
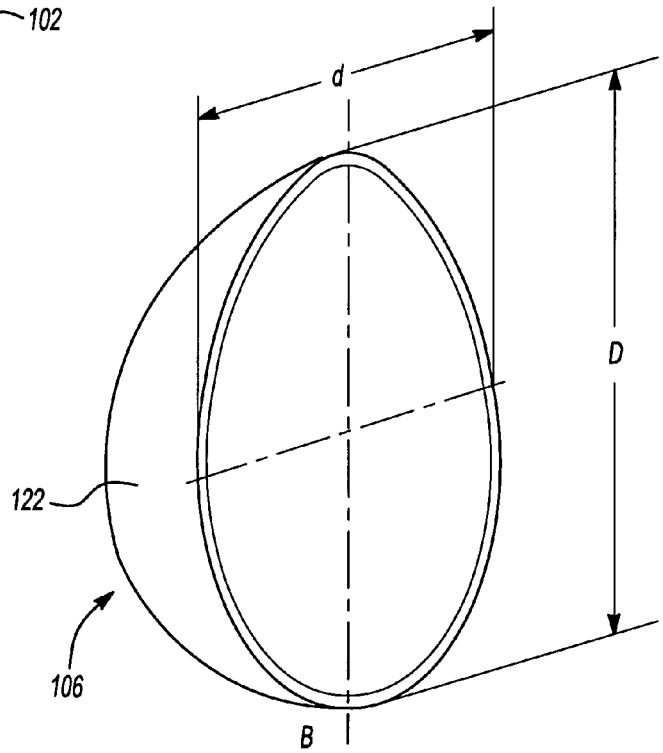
FIG. 2A is perspective view of an exemplary glenoid component for the reverse shoulder prosthesis of FIG. 1.
Figure 2B:
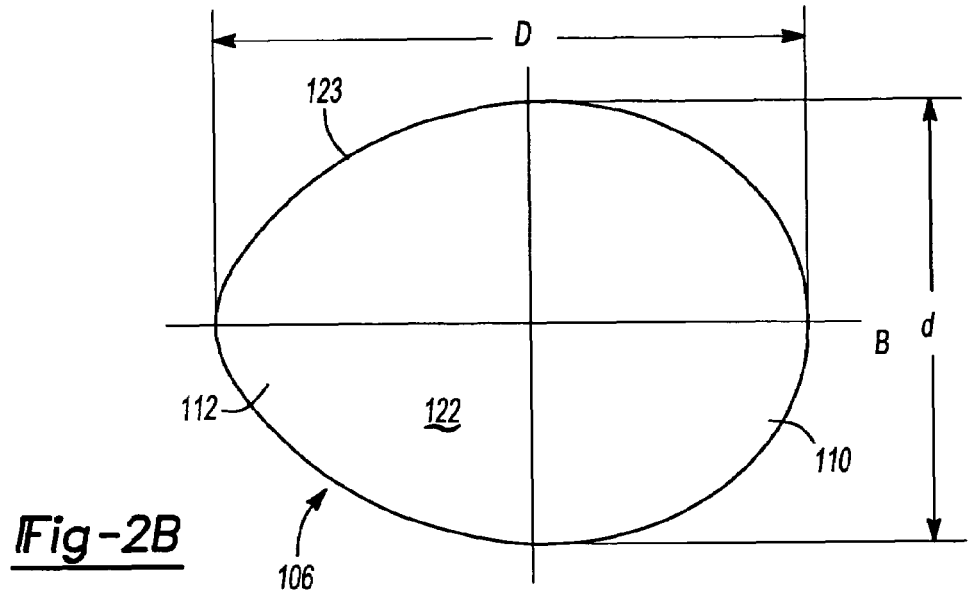
FIG. 2B is a plan view of the glenoid component of FIG. 2A.

Referring to FIGS. 1, 2A and 2B, the glenoid component 106 has a convex articulating surface 122 and a planar attachment surface 128. The convex articulating surface 122 can be ovoid (egg-shaped) and has an axis of symmetry B, a major diameter "D" along the axis of symmetry, and a minor diameter "d" orthogonal to the axis B. Referring to FIG. 2B, in plan view, the convex articulating surface 122 is bounded by an oval (egg-shaped) curve 123, which is only symmetric about the axis B. The ovoid surface 122 defines first and second ends 110, 112. Comparatively, the first end 110 is broad and the second end 112 is narrow. The glenoid component 106 can be attached to the scapula 60 using differently sized and shaped fasteners, including screws, or anchors, 126, and stabilizer pegs 124 or keels (not shown), and the like, which can be coupled directly to the glenoid component 106 or indirectly, being coupled to intermediate attachment members. The glenoid component 106 can be attached to the scapula 60 such that the broad end 110 is inferior to the narrow end 110 or conversely. The planar attachment surface 128 can oriented at an angle α relative to a direction defined by a longitudinal axis "A" of the humeral stem 102 and attached to an appropriately resected surface of the scapula 60. The angle α can be customized for the patient's anatomy, including consideration of any remaining functionality of the rotator cuff muscle 54. A non-zero angle α in the range of about 0° to 45° can reduce the magnitude of shear stress component of the stresses transmitted between the glenoid component 106 and the scapula 60, thereby reducing the risk of the glenoid component 106 loosening from the scapula 60.

Figure 3A:
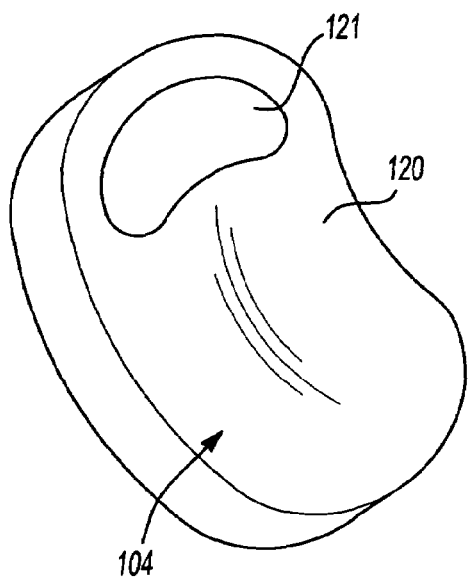
FIGS. 3A and 3B are perspective views of exemplary sockets for the reverse shoulder prosthesis of FIG. 1 illustrating optional conforming portions.
Figure 3B:
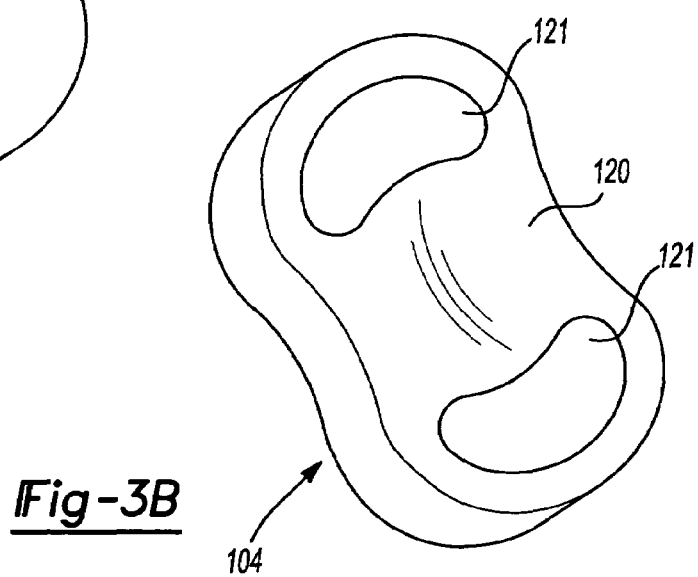

During motion of the shoulder, the ovoid articulating surface 122 of the glenoid component can partially contact the concave articulating surface 120 of the socket 104 to provide non-conforming, minimally constrained articulation. The continuously varying curvature of the ovoid articulating surface 122 allows for variable constraint between the articulating surfaces, 122, 120 by providing a degree of variable contact. Referring to FIGS. 3A and 3B, additional constraint can be optionally achieved by providing the articulating surface of the socket 104 with one or more conforming portions 121 that are constructed to conform with corresponding portions of the ovoid articulating surface 122 of the glenoid component 106. For example, minimal constraint associated with smaller contact can prevail up to a position of conformance in which a conforming portion 121 of the articulating surface 120 of the socket 104 engages the ovoid articulating surface 122. At the position of conformance, larger contact provides more constraint against a further movement that would cause the socket 104 to migrate substantially superiorly relative to the glenoid component 106 under the action of the deltoid muscle 52. Accordingly, the reverse shoulder prosthesis 100 can provide optionally a combination of relatively constrained motion for stability and relatively unconstrained motion for flexibility of the joint. The desired degree of constraint can be achieved by varying the size, shape and location of the conforming portion 121 on the socket 104.

Figure 4:
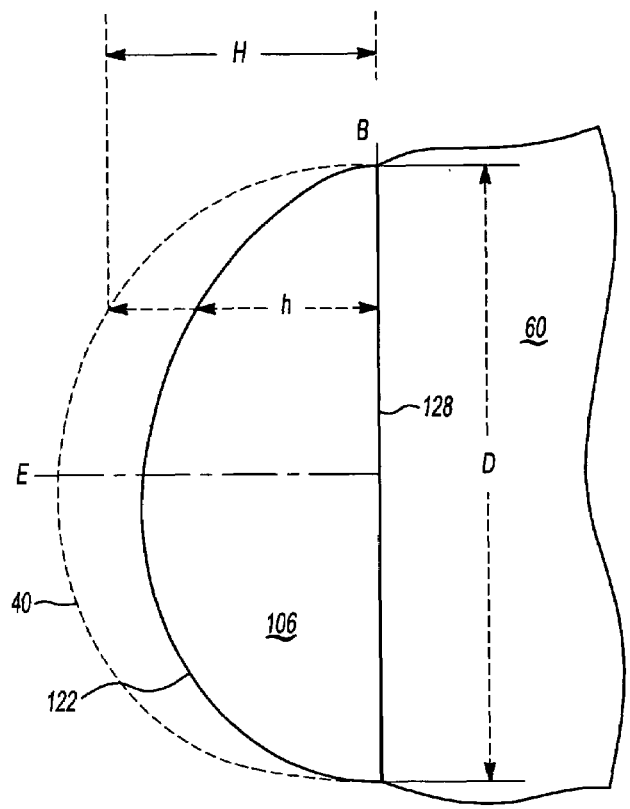
FIG. 4 is a side view comparing a prior art glenosphere with an ovoid glenoid component according to the present teachings.

Referring to FIG. 4, the exemplary ovoid surface 122 of the glenoid component 106 is not symmetric relative to a plane E that is orthogonal to the axis B and bisects the planar attachment base 128. The ovoid surface 122 has a lower profile curving away from the scapula 60 than a prior art spherical glenosphere 40 (illustrated in dashed lines) that has a diameter that is equal to the major diameter D of the glenoid component 106 along the axis B. The height h of any point of the ovoid surface 122 from the axis B is less than the height H of the corresponding prior art glenosphere 40. Furthermore, the height h is not symmetrically distributed about the axis E, in contrast to the height H of the prior art glenosphere. Accordingly, the glenoid component 106 can reduce scapular notching relatively to the prior art glenosphere 40.

Although the glenoid component 106 is illustrated as a semi-ovoid, it will be appreciated that a portion of an ovoid surface or other convex surface 122 with h less than H can also be used for the reverse shoulder prosthesis 100. Such a surface 122 may be referred as a convex surface that has a height that is less than a corresponding spherical-surface height, and can include surfaces that are ovoid (egg-shaped), ellipsoidal, pear-shaped, etc. It will also be appreciated that an ovoid surface having major diameter D and a minor diameter d can still have a variety of shapes. For example, referring to FIG. 5, the plan view curve 123 of the glenoid component 106 can be defined mathematically as a perturbation of the equation of an ellipse that has major diameter D=2a and minor diameter d=2b, using a factor f(x) which is selected such that f(0)=1:

$$\frac{x^2}{a^2} + \frac{y^2 f(x)}{b^2} = 1$$

Figure 5:
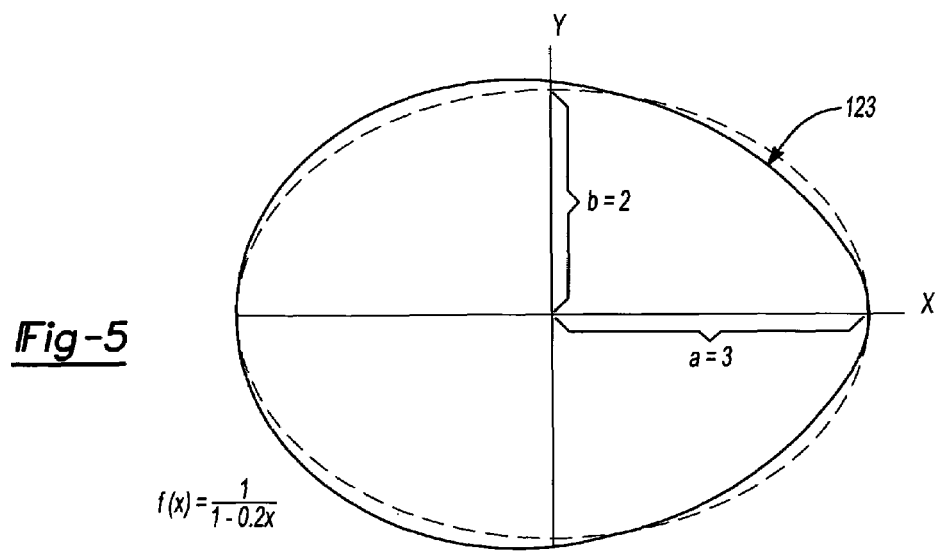
FIG. 5 is an exemplary curve defined by a plan view of the glenoid component of the present teachings shown in comparison with an ellipse.

In the example of FIG. 5, a is equal to 3 units, b is equal to 2 units and f(x) is:

$$f(x) = \frac{1}{1 - 0.2x}$$

Other egg-shaped curves can be obtained by other known mathematical methods, such by joining two halves of different ellipses, etc.

While particular embodiments have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not to be limited to the particular embodiments illustrated by the drawings and described in the specification, but that the present teachings will include any embodiments falling within the foregoing description and the appended claims.

What is claimed is:

1. A reverse shoulder prosthesis comprising:
   a humeral stem implantable in a shoulder humerus;
   a humeral socket attached to the humeral stem, the socket having a concave articulating surface defining a first shape; and
   a glenoid component including an attachment surface for attachment to the shoulder glenoid and a convex ovoid surface non-conformingly articulatable with the articulating surface of the socket, the convex ovoid surface having a narrow end and a broad end and defining a second shape, the first and second shapes not conforming relative to one another.

2. The reverse shoulder prosthesis of claim 1, wherein the narrow end is superior and the broad end is inferior.

3. The reverse shoulder prosthesis of claim 2, wherein the attachment surface is inclined at an angle relatively to a longitudinal axis of the humerus.

4. The reverse shoulder prosthesis of claim 3, wherein the angle is in the range of about 0° to 45°.

5. The reverse shoulder prosthesis of claim 3, wherein the angle is selected for reducing loosening of the glenoid component.

6. The reverse shoulder prosthesis of claim 3, wherein a shape of the ovoid surface is selected for reducing notching of the humeral stem on the scapula.

7. The reverse shoulder prosthesis of claim 2, wherein the ovoid surface has a variable curvature.

8. The reverse shoulder prosthesis of claim 1, further including at least one threaded fastener and at least one unthreaded fastener for attaching the glenoid component to the scapula.

9. The reverse shoulder prosthesis of claim 1, wherein the humeral socket is modular and includes a modular backing plate and a modular insert.

10. A reverse shoulder prosthesis comprising:
    a humeral socket attachable to a shoulder humerus, the humeral socket having a concave surface defining a first shape; and
    a glenoid component attachable to the shoulder glenoid, the glenoid component having a major diameter and a convex surface for articulating with the concave surface of the socket, the convex surface having a height from the major diameter that is less than a corresponding height of a spherical surface having the same a diameter equal to the major diameter, the convex surface having a broad end and a narrow end and defining a second shape, the first and second shapes only partially conforming.

11. The reverse shoulder prosthesis of claim 10, further comprising a humeral stem attached to the humeral socket.

12. The reverse shoulder prosthesis of claim 11, wherein the glenoid component has a planar attachment surface oriented at an angle relative to a longitudinal axis of the humeral stem.

13. The reverse shoulder prosthesis of claim 12, wherein the angle is selected for reducing loosening of the glenoid component.

14. The reverse shoulder prosthesis of claim 11, wherein the humeral socket is integral with the humeral stem.

15. The reverse shoulder prosthesis of claim 10, wherein the humeral socket is modular.

16. The reverse shoulder prosthesis of claim 15, wherein the humeral socket comprises a backing plate and an insert.

17. The reverse shoulder prosthesis of claim 10, wherein the convex surface is an ovoid surface.

18. The reverse shoulder prosthesis of claim 10, wherein the humeral socket is an integral component.

19. The reverse shoulder prosthesis of claim 10, wherein the concave surface of the humeral socket has a radius of curvature selected from the group consisting of constant curvature, variable curvature, and combinations thereof.

20. The reverse shoulder prosthesis of claim 10, wherein the glenoid component further comprises scapula attachments selected from the group consisting of screws, anchors, pegs, keels, and combinations thereof.

21. The reverse shoulder prosthesis of claim 20, wherein the scapula attachments are directly coupled to the glenoid component.

22. The reverse shoulder prosthesis of claim 20, wherein the scapula attachments are indirectly coupled to the glenoid component.

23. The reverse shoulder prosthesis of claim 10, wherein the first shape includes a single isolated conforming portion that conforms to and contacts a corresponding portion of the second shape during a relative articulation motion between the convex and concave surfaces, the single isolated portion surrounded by non-conforming portions of the concave surface.

24. The reverse shoulder prosthesis of claim 23, wherein an articulation constraint between the convex and concave surfaces is minimal before contact starts over the single isolated conforming portion, and wherein the articulation constraint increases when contact of the first and second shapes begins over the single isolated conforming portion.

25. The reverse shoulder prosthesis of claim 23, wherein the single isolated conforming portion provides variable amount of constraint during articulation of the convex and concave surfaces.

26. The reverse shoulder prosthesis of claim 23, wherein the single isolated conforming portion is offset relative to a minor diameter of the second shape.

27. The reverse shoulder prosthesis of claim 10, wherein first shape includes at least two isolated and spaced apart conforming portions that conform to and contact corresponding portions of the second shape during a relative articulation motion between the convex and concave surfaces.

28. The reverse shoulder prosthesis of claim 27, wherein an articulation constraint between the convex and concave surfaces increases when contact of at least one of the first and second shapes begins over the corresponding isolated conforming portion.

29. The reverse shoulder prosthesis of claim 27, wherein the two isolated conforming portions provide variable amount of constraint during articulation of the convex and concave surfaces.

30. The reverse shoulder prosthesis of claim 27, wherein the two isolated conforming portions are offset relative to a minor diameter of the second shape.

* * * * *